(12) United States Patent
Kim et al.

(10) Patent No.: US 6,986,908 B2
(45) Date of Patent: Jan. 17, 2006

(54) DELTA-AMINOLEVULINIC ACID FOR PREVENTION AND TREATMENT OF INFECTION BY PATHOGENIC MICROORGANISMS AND PARASITE

(76) Inventors: Hyeungrak Kim, #102-403, Samick Green APT, Daeyoun3-dong, Nam-gu, Pusan-city, 606-023 (KR); Jaeho Kim, #5-103, Shindonga APT, Sachon-dong, Chungju-city, Choongchungbuk-do, 360-220 (KR); Myungjoo Oh, #12-1504, Kumho APT, Shinwol-dong, Yosoo-city, Chullanam-do, 550-190 (KR); Daeseok Byun, #103-202, Sunkyung APT, Yonsan8-dong, Yonje-gu, Pusan-city, 611-088 (KR)

( * ) Notice: Subject to any disclaimer, the term of this patent is extended or adjusted under 35 U.S.C. 154(b) by 567 days.

(21) Appl. No.: 09/793,707

(22) Filed: Feb. 27, 2001

(65) Prior Publication Data
US 2001/0053796 A1    Dec. 20, 2001

(30) Foreign Application Priority Data
May 8, 2000    (KR) .............................. 2000-24382

(51) Int. Cl.
A23B 7/10        (2006.01)
A23L 1/20        (2006.01)
A61K 47/00       (2006.01)

(52) U.S. Cl. .................. 426/53; 426/54; 426/630; 424/439

(58) Field of Classification Search ............... 424/400, 424/405, 439, 442; 426/53, 54, 630
See application file for complete search history.

(56) References Cited

U.S. PATENT DOCUMENTS

| | | | |
|---|---|---|---|
| 5,484,803 A * | 1/1996 | Richter ..................... | 514/410 |
| 5,895,786 A * | 4/1999 | Ben-Hur et al. ............ | 514/561 |
| 5,955,490 A * | 9/1999 | Kennedy et al. ........... | 424/9.61 |
| 6,323,012 B1 * | 11/2001 | Ben-Hur et al. ......... | 435/173.1 |

* cited by examiner

Primary Examiner—Thurman K. Page
Assistant Examiner—Isis Ghali
(74) Attorney, Agent, or Firm—Nath & Associates PLLC; Gary M. Nath; Lee C. Heiman

(57) ABSTRACT

The present invention relates to a composition containing a δ-aminolevulinic acid as effective dose for prevention and treatment of infection by pathogenic microorganisms and parasite. More particularly, it refers to the composition for prevention and treatment through cultivation of fish in a water tank containing δ-aminolevulinic acid or the oral administration of a feed mixed with δ-aminolevulinic acid to fish.

2 Claims, 2 Drawing Sheets

DELTA-AMINOLEVULINIC ACID FOR PREVENTION AND TREATMENT OF INFECTION BY PATHOGENIC MICROORGANISMS AND PARASITE

BACKGROUND OF THE INVENTION

1. Field of the Invention

The present invention relates to a composition containing a δ-aminolevulinic acid as effective dose for prevention and treatment of infection by pathogenic microorganisms and parasite. More specifically it refers to the composition for prevention and treatment through cultivation of fish in a water tank containing δ-aminolevulinic acid or the oral administration of a feed mixed with δ-aminolevulinic acid to fish.

2. Description of the Prior Art

Recently, with the technical development of artificial seedling production of fish, the cultivation industry is rapidly increasing. Thus, high quality fish such as a flatfish (*Paralichyhus olivaceus*), rockfish (*Sebastes schoegeli* Hilgendorf), Red seabream (*Pagrus major*), a swellfish are in the spotlight as cultivation fish. Due to this rapid expansion of the cultivation industry, the environment, such as the Korean coastal seawaters, are always in danger of generating diseases with the probability that it could be polluted by pathological bacteria such as Herpesvirus, Birnavirus, Rhabdovirus, which are main pathological viruses and *Edwardsiella* sp., *Vibrio* sp., *Staphylococcus* sp., *Streptococcus*, *Flexibacter* sp., which are pathological bacteria. (Cheung, R. J., Nigrelli, R. F. and Ruggieri, G. D. 1980. Studies on the morphology of uronema with a description of the infection in marine fish, J. Fish Disease, 3; 295; Drolet M., Peloguin L., Escelard Y., Cousineau L., and Sasarman A., 1989. Isolation and nucleotide sequence of the hemA gene of *E. coli* K-12, Mol. Gen. Genet, 216; 347: Ellen, N. L, and Kaplan S., 1993. 5-Aminolevulinic acid availability and control of spectral complex formation in hemA and hemT mutant of R. spharoides, J. Bacteriol., 175; 2304) and the cultivating industry have been seriously damaged by this pathological infection. Damage caused by pathological bacteria and virus infections of seedling production is worse than that of adult fish cultivation, which also has been increasing yearly. For the prevention and treatment of these bacterial diseases, antibiotics for veterinary use have been currently applied. Over-administration of improper antibiotics in an attempt to cure the diseases caused by unidentified pathological bacteria increases the cost of cultivating fish. It may also result in the emergence of bacteria having new tolerances because of the new antibiotics, and thereby delaying the experimental time and preventing prompt treatments. Accordingly, feed supplement for increasing the vitality or immunity of cultivating fish has been in development since the mass mortality rate of cultivating fish is increasing.

As explained above, among the marine fish diseases attacking in Korea, besides microorganism and viruses, serious damaging diseases caused by parasites such as *Ichthyophthirius* or the symptom of infection of *Ichthyophthirius multiphilis*, which is a kind of ciliate, and scuticociliatoisis by Scuticociliatida are also present. In Japan, a study on formalin digestion method, which is often used as a prevention method of parasitic diseases has been conducted. However, in the case of exposed imagoes, application to cultivation site, which was based on the report (Yoshinaga, T. and Nakazoe, J. 1993. Isolation and in vitro cultivation of an unidentified ciliate causing scuticociliatoisis in Japanese flounder, Fish Pathol., 28; 131) that the activity at digestion concentration of around 100 ppm was decreased, has shown that the experimental result showing no effect at all, is hard to be applied to (Mizuno, Y., 1993. Control methods of diseased flounder used in fish farm in Japan, J. Fish Pathol., 6; 219). This was carried out by the infectious disease prevention team of the cultivation site. Scutica proliferation method using cell culture method in the laboratory was a successful and confirmed pathogenicity thereof by applying to a flatfish using Scuticociliatida on cell culture. Removing the activity of imagoes by using Frezil and Actecin as a method for inactivation thereof in vitro was also a success, but there has not been any studies on inactivating infectious imagoes within the fish body (Yoshimizu, M., Hyuuga, S., Oh, M.-J., Ikoma, M., Kimura, T., Mori, T., Nomura, T., and Ezura, Y. 1993. Scuticociliatida infection of cultured hirame-characteristics, drug sensitivity and pathogenicity of cultured scuticocilliatida, J. Fish Pathol., 6; 205). There has not been any effects, as a result of the test for treatment effects using cultivating flatfish, fry and intermediary rearing fish in Korea and in the same manner of the study of Mizuno (Mizuno, Y., 1993. Control methods of diseased flounder used in fish farm in Japan, J. Fish Pathol., 6; 219) and Yoshimizu (Yoshimizu, M., Hyuuga, S., Oh, M.-J., Ikoma, M., Kimura, T., Mori, T., Nomura, T., and Ezura, Y. 1993. Scuticociliatida infection of cultured hirame-characteristics, drug sensitivity and pathogenicity of cultured scuticocilliatida, J. Fish Pathol., 6; 205) as the reason showing no treatment effect within the body, it is possible to remove Scutica exposed to the basin system same as in the case of formalin treatment. However, it has shown that it's not effective since a series of experimental drugs could not permeate into the body. It is not economical compared with cheap formalin in case of removing only discharged imagoes, because the price of the drug is much higher than that of general marine drugs. Pathological study by infection of parasite has been conducted in Korea (Lee, H.-S. and Sinskey, A. J. 1994. Molecular characterization of aceB, a gene encoding malate synthase in *Corynebacterium glutamicum*, J. Microbiol. Biotechnol., 4; 256) and it has shown that infection of imagoes causes fatal damage by passing through the epidermis and branchiae along the blood flow and attacking the nervous system within the body. This pathological phenomenon is similar to the result of studies on fry of flatfish (Cheung, R. J., Nigrelli, R. F. and Ruggieri, G. D. 1980. Studies on the morphology of uronema with a description of the infection in marine fish, J. Fish Disease, 3; 295) and freshwater fish (Hoffman, G. L. 1955. A disease of freshwater fish caused by tetrahymena and a key for identification of holotrich ciliates of freshwater fish, J. Parasitol., 61; 217).

Recently, with the rise of the problem of environmental pollution resulting from toxicity by overuse of chemical synthetic insecticide and herbicide, there has been a need for finding biological, particularly, microorganism-originated new materials. In light of this, δ-aminolevulinic acid has widely reported as biosynthetic precursors of tetrapyrrole compounds such as heme, bacteriochlorophyll, corrinoid, as photodynamic material which is the only known biological material, as herbicide, insecticide, plant growth stimulator and cancer cure (Hua, Z., Scott, L. G., Thomas, H. F., and Russell, H., 1995, Effectiveness of delta-aminolevulinic acid induced protoporphyrin as a photosensitizer for photodynamic therapy in Vivo, Cancer Research, 55; 1723; Matsumoto, T. H., Usui, K., and Ishizuka, K. 1992, Basis of Differential Tolerance of Plant Species to delta-Aminolevulinic Acid, Weed Research, 37; 60; Matsumoto, H., Tanida, Y., and Ishizuka, K. 1994. Porphyrin Intermediate Involved in Herbicidal Action of delta-Aminolevulinic Acid on Duckweed, Pesticide Biochemistry, 48; 214; Rebeiz, C. A, Juvik, J. A., and Reibez, C. C. 1988. Porphyric insecticides: Concept and phenomenology, Pestic. Biochem. Physiol., 30; 11; Tanaka, T., Takahashi, K., Hotta, Y., Takeuchi, Y., and Konnai, M., 1992. 5-aminolevulinic acid as plant growth stimulator, Eur. Pat. Appl. EP514 776). Also, δ-aminolevulinic acid has been regarded as an eco-friendly herbicide and insecticide because it is easily biodegradable. However, the quantity of δ-aminolevulinic acid produced in microorganism has low concentration and the industrialization of chemical synthetic production is also difficult owing to the complicated synthetic process (Beale, S. I., Gold, M. H., and Granick, S., 1979, Chemical synthesis of 4,5-dioxavaleric acid and its non-enzymatic transamination to 5-aminolevulinic acid, Phytochemistry, 18; 441). Therefore, highly toxic synthetic photodynamic herbicides, such as diphenyl ethers (DPEs) and oxadiazole are being produced by chemical synthesis. The problem of environmental pollution has brought up the harmfulness of these synthetic photodynamic herbicides. For example, contamination of water supply sources and damage of neighbors resulting from the overuse of herbicide in golf links have been raised as a social issue.

Once δ-aminolevulinic acid, which is specifically produced from Rhodobacter, is sprayed on plants, it acts on only dicotyledon selectively and then pchlide, strong oxidizing material, is formed through sunlight. Therefore, a series of oxidation reactions take place and lead to weed-killing activity, which destroys phospholipid of leaves and causes them to wither. Therefore, δ-aminolevulinic acid does not damage people, animal nor crop, only withering weeds selectively (Rebeiz, C. A., Montazer-Zouhoor, A., Hopen, H., and Wu, S. M., 1984. Photodynamic herbicides. Concept and phenomology, Enzyme Microb. Technol., 6; 390) and has been reported as eco-friendly herbicides (Rebeiz, C. A, Juvik, J. A., and Reibez, C. C. 1988. Porphyric insecticides: Concept and phenomenology, Pestic. Biochem. Physiol., 30; 11). However, δ-aminolevulinic acid is unprofitable since organic synthesis requires a complicated multi-step processes and the unit cost of production is high. Most of herbicides used currently have problems such as high toxicity to humans and high soil-toxicity (Beale, S. I., Gold, M. H., and Granick, S., 1979, Chemical synthesis of 42,5-dioxavaleric acid and its non-enzymatic transamination to 5-aminolevulinic acid, Phytochemistry, 18; 441).

The importance of food had been traditionally considered as a sequence of nutrition, flavor and safety. However, with the interests in increasing the national income and health, food safety has moved to the forefront. In regards to food safety, the pathogenic microorganism contaminated or mixed in foods, heavy metals, agricultural chemicals and antibiotics are most frequently raised. In case of cultivating fish, antibiotics remaining within the tissue of fishes, which resulted from over-administration, may decrease food safety. Pathogenic diseases occur frequently in accordance with the coastal contamination and congested nurseries. Due to rash administration of drugs in order to cure these diseases, new pathogenic microorganism having new drug-tolerance will appear and consequently, the development of new antibiotic is in high demand. To cure fishery diseases, as in medical science, development of more varied antibiotics can improve the productivity of cultivating fish but it may cause problems in the matter of food safety. Therefore, from seedling production nursery of cultivating fish to adult fish nursery, there is demanded for the development of new materials, which can widely prevent or cure diseases caused by pathogenic microorganisms.

SUMMARY OF THE INVENTION

With this background in mind, the present inventors cultivate fish, without using antibiotics, by providing fish or fish tanks with fish feed including δ-aminolevulinic acid, to thereby prevent infection by pathogenic microorganism and parasite and, in the case of already infected fishes, show the effect of treatment.

Therefore, it is an object of the present invention to provide a composition containing a δ-aminolevulinic acid as an effective ingredient for prevention and treatment of infection by pathogenic microorganisms and parasite.

It is another object of the present invention to provide a method for prevention and treatment of infection by pathogenic microorganisms and parasite by orally administering the composition to fishes or administering it to a fish tank on cultivating.

It is another object of the present invention to provide feed for cultivating fishes containing a δ-aminolevulinic acid as an effective ingredient.

In order to accomplish the above objects, the present invention provides a composition, which is useful for the prevention and treatment of infection by pathogenic microorganisms and parasite, comprising a δ-aminolevulinic acid as an effective ingredient.

Preferably the pathogenic microorganism is selected from the group consisting of *Edwardsiella tarda, Streptococcus* sp., *Staphylococcus* sp., *Staphylococcus epidermidis, Pseudomonas* sp. and *Vibrio anguillarum.*

Another embodiment of this invention provides a method of preparing the composition for prevention and treatment of infection by pathogenic microorganisms and parasite, by adding the composition to a fish tank at a concentration of 0.01~10 ppm as preparation.

A further embodiment of this invention provides a method of preparing the composition for prevention and treatment of infection by pathogenic microorganisms and parasite, comprising the steps of adding the composition to common fish-cultivating feed at a concentration of 0.1~10 ppm; and orally administering the feed to fish.

A further embodiment of this invention provides a composition, which is useful of prevention and treatment of infection by irido virus, comprising a δ-aminolevulinic acid in effective ingredient.

A further embodiment of this invention provides a method of preparing the composition for treatment of infection by irido virus, comprising the steps of adding the composition to fish-cultivating feed at a concentration of 0.1~10 ppm; and
    administering the feed to fish cultivating water tanks.

A further embodiment of this invention provides a composition, which is useful for prevention and treatment of infection by Scutica, comprising of a δ-aminolevulinic acid as an effective ingredient.

A further embodiment of this invention provides a method of preparing the composition for treatment of infection by Scutica, comprising the steps of adding the composition to fish-cultivating feed at a concentration of 0.01~10 ppm; and administering the feed to fish cultivating water tank.

A further embodiment of this invention provides a method of preparing the composition for treatment of infection by Scutica, comprising the steps of adding the composition to fish-cultivating feed at a concentration of 0.1~100 ppm; and orally administering the feed to fish.

A further embodiment of this invention provides a feed of fish nursery, wherein δ-aminolevulinic acid, at a concentration of 0.1~100 ppm, is included.

BRIEF DESCRIPTION OF THE DRAWINGS

The above object of the present invention will be more clearly understood from the following detailed descriptions taken in conjunction with the accompanying drawings, in which.

DETAILED DESCRIPTION OF THE PREFERRED EMBODIMENTS

Figure 1:
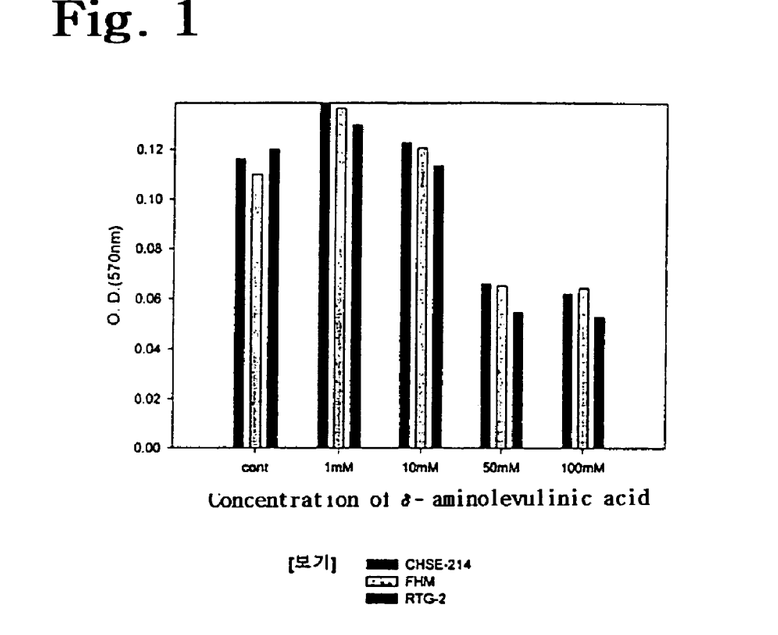
FIG. 1 is a bar graph showing the cell toxicity effects of fish cell line according to the contents of δ-aminolevulinic acid.
Figure 2A:
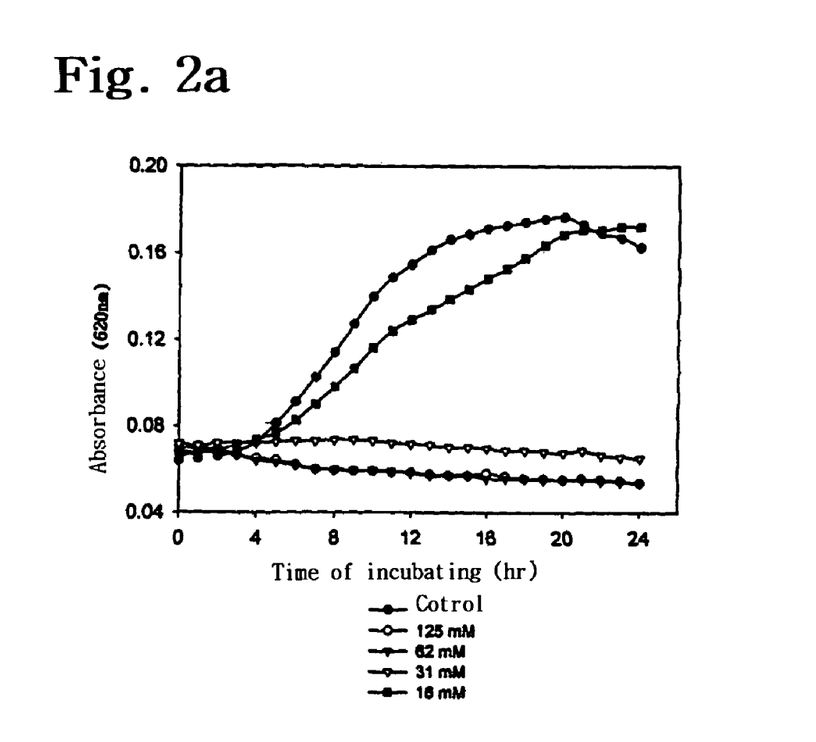
FIGS. 2a and 2b illustrate the proliferation inhibiting effects of pathogenic microorganisms such as *Edwardisiella trada* and *Staphylococcus* sp. according to the contents of δ-aminolevulinic acid for market.
Figure 2B:
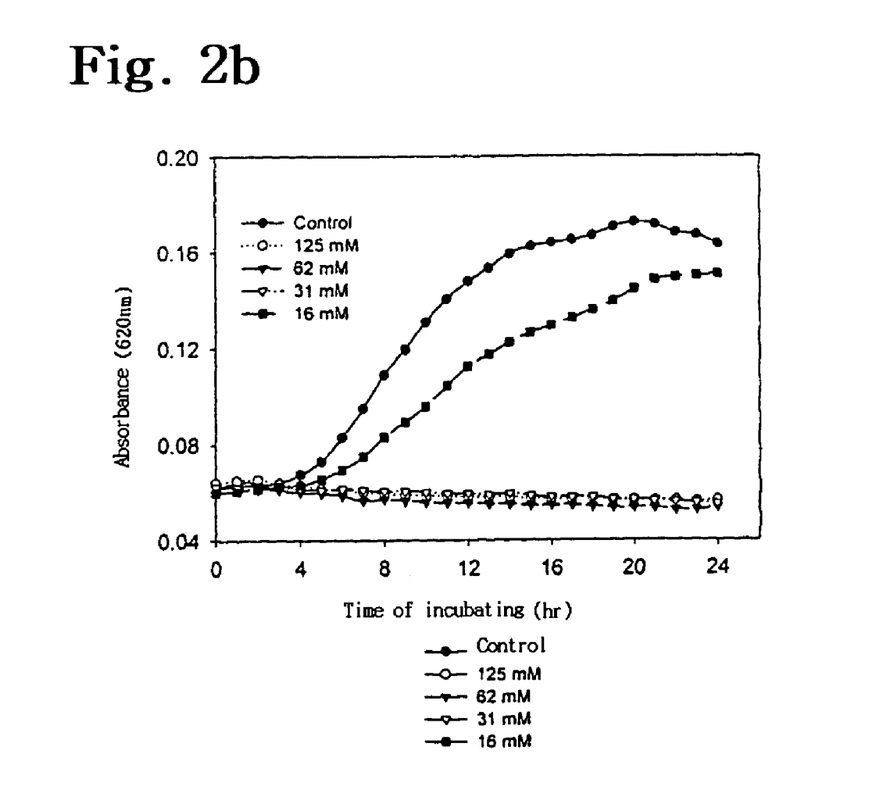

Hereinafter, the detailed description of the present invention will be taken into account more definitely in accordance with the following examples and experiment.

EXAMPLE 1

Cell Toxicity of δ-aminolevulinic Acid for Fish Cell Line

In this example, primary experiment was conducted in order to ascertain toxicity of δ-aminolevulinic acid as prevention and cure for infection by numerous kinds of fish pathogenic bacteria, virus and Scutica. For three kinds of fish-originated cell line, toxicity within cell systems in vitro was investigated and safe concentration of δ-aminolevulinic acid treatment and toxic concentration were ascertained. Concentration of δ-aminolevulinic acid having no effect on fish cells was established to examine δ-aminolevulinic acid toxicity for fish cells by direct exposure.

δ-aminolevulinic acid feed were prepared to 1.0 M concentration (0.167 g/mL HBSS) and diluted by 10-fold dilution method. 100 μl of each fish cell line suspension of $2.5 \times 10^5$ were placed into 96-well microplate and then, 100 μl of each of the resulting diluted solution, 4 well/dilution unit, were added respectively. Fish cell lines, which were used for this cell toxicity experiment of δ-aminolevulinic acid, were RTG-2 (Rainbow Trout Gonad), FHM (Fathead Minnow Epithelioma) and CHSE (Chinook Salmon Embryo) lotted out from Dr. M. Yoshimizu of the Department of Fisheries, Hokkaido University, Japan. For these experimental cells, 100 U/mL penicillin (Sigma), 100 μl/mL streptomycin (Sigma) and MEM media supplemented with 5% fetal bovine serum (FBS, Gibco) for cell culture were used. Cultured cells in 96-well microplate was incubated for 3 hrs at 15° C. and δ-aminolevulinic acid were added to wells at amounts of 100 μl of 0, 1.0, 10, 50 and 100 mM and incubated for 24 hrs at 18° C. As a control group, instead of δ-aminolevulinic acid, HBSS was added at the same amount. After incubation, 5 mg/mL of MTT solution [3-(4, 5-dimethylthiazol-2-yl)-2,5-diphenyl tetrazolium bromide (DOJINDO Lot ZY903, Japan) was dissolved in PBS and filtered (0.45 μm) and used for this experiment were added to each well, 100 μl respectively and 0.04 N HCl-isopropanol was added, 100 μl respectively. Absorbance was measured with an ELISA reader at 570 nm. As shown in Table 1, when three species of cell lines used in these experiments were treated with 1 mM, 10 mM of δ-aminolevulinic acid, it has shown similar cell proliferation levels, compared to the control group. Whereas, it has shown half of the cell proliferation level compared to control group, when 50 mM, 100 mM of δ-aminolevulinic acid was used. As a result, the safe range of toxicity has shown to be below 10 mM, considering reaction condition within wells of cell culture condition, and the optimum concentration standard for experiments was determined. Also, it has shown that direct toxicity was not shown within the fish body if the treatment concentration of this substance set to be below 50 mM, when the pathway to target organ or cell unit by interior absorption and metabolic process of substance was estimated (generally the absorption rate within fish body is 10~20%), as basic data for the determination of the toxic concentration according to δ-aminolevulinic acid application within the living body.

EXAMPLE 2

Cell Toxicity of δ-aminolevulinic Acid for Fish

From the result of δ-aminolevulinic acid toxicity experiment in cell unit in Example 1, the toxicity to cell by exposure for 24 hrs has shown to be safe below 50 mM concentration. In this example, in order to examine the toxicity of fish body by internal injections of δ-aminolevulinic acid, 2 methods were used; direct administration using injection and, digestion method, which is most easily used as drug administration method for multitude of fish body in fish farms generally.

As experimental fish, fry of Bastardhalibut (3 g), *Pagrus major* (1.5 g) and *Sebastes schlegeli* (5 g) were used to investigate toxic effects. Treatment concentration 500, 100, 50 and 10 mM of δ-aminolevulinic acid solution were prepared and 100 μl of each was injected into each fish body abdominally. The fish were put into a fish tank and observed for one week. Also, 167.6 ppm of δ-aminolevulinic acid was prepared by dissolving 5.028 g of δ-aminolevulinic acid in 30 L of breeding seawater, for experiments by digestion method. Experimental seawater was prepared containing 16.76 ppm and 1.676 ppm, 10-fold and 100-fold dilution respectively, of δ-aminolevulinic acid with the same method. After experimental fishes were exposed for 10, 30, 60, 120 and 180 min in each fish tank, 20 of the fish were picked at each exposing time and moved to fish tanks without δ-aminolevulinic acid, where the viability was measured for one week. From the result of experiment, as shown in Table 1, groups treated with δ-aminolevulinic acid by abdominal injection have not shown any changes in viability among all fish body and species, without reference to the concentration of δ-aminolevulinic acid. As shown in Table 1, groups treated with δ-aminolevulinic acid by digestion method have shown 100% of viability in all control groups and treated groups and no differences among species, concentration and digestion time. As a result, no direct toxicity for fish body has found within the applicable concentration range, which was considered using form and economical efficiency for direct application of δ-aminolevulinic acid to fish. In abdominal injection, in the case of Bastardhalibut, it has not shown any toxicity when injected at a concentration of below 50 mM and below 3.3% of body weight and in the case of *Pagrus major* and *Sebastes schlegeli*, it has not shown any toxicity when injected at a concentration of below 50 mM and below 2.0% of body weight. In the case Bastardhalibut, *Pagrus major* and *Sebastes schlegeli* being digested at 167 ppm for up to 180 min, no toxicity for experimental fish were shown. Therefore, it has shown that, as a fish disease treatment and prevention, it does no harm to Bastardhalibut, Pagrus major and Sebastes schlegeli below the said concentration.

TABLE 1

Viability of fry of Bastardhalibut, Pagrus major and Sebastes schlegeli according to δ-aminolevulinic acid abdominal injection (%)

| Fish species | 50 mM | 10 mM | 5 mM | 1 mM | Control |
|---|---|---|---|---|---|
| Bastardhalibut | 100% | 100% | 100% | 100% | 100% |
| Chrysophrys major | 100% | 100% | 100% | 100% | 100% |
| Sebastes schlegeli | 100% | 100% | 100% | 100% | 100% |

TABLE 2

Viability of fry of Bastardhalibut, Pagrus major and Sebastes schlegeli according to δ-aminolevulinic acid digestion (%)

| Fish species | 167 ppm 10~180 min | 16.7 ppm 10~180 min | 1.67 ppm 10~180 min | 1.67 ppm 10~180 min | 0.167 ppm 10~180 min |
|---|---|---|---|---|---|
| Bastardhalibut | 100% | 100% | 100% | 100% | 100% |
| Chrysophrys major | 100% | 100% | 100% | 100% | 100% |
| Sebastes chlegeli | 100% | 100% | 100% | 100% | 100% |

EXAMPLE 3

Proliferation Effect of Marine Pathogenic Microorganisms by δ-Aminolevulinic Acid In Vitro Experiment 1: Proliferation Effect for Marine Pathogenic Bacteria Pathogenic index bacteria used in this experiment are *Edwardsiella tard, Streptococcus* sp., *Staphylococcus* sp., *Staphylococcus epidermidis, Pseudomonas* sp., *Vibrio anguillarum* which are collected from the marine fish farm nearby Yeosu. In solid culture, they were cultured in TSA (tryptic soy agar) supplemented with 0.2% NaCl flat media and in liquid culture, they were prepared by culturing in BHI broth for 24 hrs and setting the O.D. value as 1.0. δ-aminolevulinic acid used in this experiment were one on the market (Sigma) and one formulated by inventors of the present invention (Korean patent application No. 1998-41898). Each 0.167 g δ-aminolevulinic acid were dissolved in 1.0 mL sterilized distilled water was used as undiluted solution. 1.0 M δ-aminolevulinic acid was 2-fold diluted with BHI broth by stages up to 64-fold and prepared for test solution to examine pathogenic bacteria proliferation-pro-hibiting effect. In 96-well microplate, diluted δ-aminolevulinic acid by stages and bacteria suspension are mixed as ratio of 1:1 and growth of bacteria was observed with ELISA reader set to 620 nm at 25° C. for 24 hrs according to δ-aminolevulinic acid concentration. In control group, instead of δ-aminolevulinic acid, BHI broth bacteria suspension were mixed with (1:1) and then observed with the same method above. MIC assay by δ-aminolevulinic acid for major pathogenic bacteria of marine cultivating fishes, *Edwardsiella tard, Streptococcus* sp., *Staphylococcus* sp., *Staphylococcus epidermidis, Pseudomonas* sp., *Vibrio anguillarum* was carried out by flat drug disc method. 100 µL of each bacteria in a culture solution was mixed with fixed amount of top agar and coated to TSA agar. 1.0 M δ-aminolevulinic acid solution was diluted by 2 folds in PBS and 10 µL of each dilution were absorbed to sterilized disc. After incubation at 23~25° C. for 2~3 days, antibacterial effect was indicated by measuring the size (mm) of clear zone. In control group, PBS was absorbed into disc instead of δ-aminolevulinic acid dilution solution with the same amount and observed. From the result of this experiment using δ-aminolevulinic acid on the market, proliferation-inhibiting effects of pathogenic bacteria according to δ-aminolevulinic acid concentration are shown in Table 2a (*Edwardsiella tard*) and Table 2b (*Streptococcus* sp.). Below 1/32 fold (31 mM) of δ-aminolevulinic acid dilution rate, proliferation of both bacteria was inhibited. However, above 1/64 fold (16 mM) of the dilution rate, there was no significant difference from the control group. The experimental result of δ-aminolevulinic acid prepared by the inventors has shown in Table 3 and no difference in effects from δ-aminolevulinic acid on the market.

TABLE 3

MIC results of pathogenic bacteria of marine cultivating fishes by δ-aminolevulinic acid

| Bacteria | MIC |
|---|---|
| *Edwardsiella tarda* | 56.0 µg/mL |
| Staphylococcus sp. | 72.9 µg/mL |
| Staphylococcus sp. | 59.6 µg/mL |
| Staphylococcus epidermidis | 62.0 µg/mL |
| Pseudomonas sp. | 42.2 µg/mL |
| *Vibrio anguillarum* | 29.9 µg/mL |

Experiment 2: Extermination Effect for Marine Pathogenic Virus

In this experiment, change of infection value by virus according to δ-aminolevulinic acid treatment was examined by $TCID_{50}$ using fish cell line for marine birnavirus (MABV) which infects major marine cultivating fish species, Bastardhalibut, Pagrus major and Sebastes schlegeli and acts as a cause for mass mortality. The virus used in this experiment was isolated from Bastardhalibut of a fish farm nearby Yeosu. Virus infection value was checked in CHSE-214 cell and then used as experimental virus solution. Virus incubation solution and δ-aminolevulinic acid diluted solution were combined with same amount (8 mL) and reacted for 30 min. and then, inoculated to culture cell and incubated at 20° C. Temporary change of virus infection value was compared with that of HBSS reaction virus solution (control). As a result, as shown in Table 4, MABV was inactivated by δ-aminolevulinic acid treatment within culture cell system.

TABLE 4

Change of Infection value by MABV according to δ-aminolevulinic acid treatment

| | Time after inoculation(days) | | | | |
|---|---|---|---|---|---|
| | 0 | 1 | 3 | 5 | 7 |
| δ-aminolevulinic acid (8 mM) | 4.3* | 3.8 | 3.5 | 2.3 | <1.8 |
| Control (HBSS) | 4.5 | 4.8 | 6.8 | 8.5 | 8.8 |

Log $TCID_{50}$/mL

EXAMPLE 4

Proliferation Effect of Marine Pathogenic Microorganisms by δ-Aminolevulinic Acid In Vivo Experiment 1: Toxicity by Administering to Fish Tanks and Administering Orally to Fishes 20 of around 25 g Bastardhalibut were bred in circulatory filtering system set as a control group and experiment group. In group 1, δ-aminolevulinic acid was administered into a fish tank once in 3 days and fish were bred for 1~3 weeks maintaining δ-aminolevulinic acid concentration as 0.1~10 ppm. In group 2, to 1 kg artificial assorted feed (EP, 3% of fish body weight: 15 g) δ-aminolevulinic acid was added, by spraying, as concentration of 0.1~100 ppm and then dried. Fish were bred for 1~3 weeks with oral administration therein. For group 1 and non-treated group, artificial assorted feed on the market, in the same amount of feed of group 2 was used without δ-aminolevulinic acid treatment. Used fish pathogenic bacteria were sterilized on 2 L triangular flasks where 1 L of Brain Heart Infusion (BHI) broth media was placed. Fish pathogenic bacteria were made by inoculating *Edwardsiella tarda, Streptococcus* sp., *Staphylococcus* sp., *Staphylococcus epidermis, Pseudomonas* sp. and *Vibrio anguillarum* into BHI broth of each flask and then was administered shake culturing for 3 days. Artificial infection of pathogenic bacteria was carried out after 3 weeks of experimental breeding. For artificial attack method, incubated bacteria were diluted in a physiological salt solution and $10^5$ CFU per 1 fish were injected by direct abdominal injection (injection dose 300 μL/fish). Artificial-infected experimental fishes of each group were moved to fish tanks for monitoring and monitored for 2 weeks for infection and mortality according to infection therein. The water temperature was maintained at 20° C. (±2° C.) throughout the experiment. As shown in Table 5, there was no mortality shown in both group 1, whose δ-aminolevulinic acid concentration was maintained at 10 ppm during breeding and group 2, where δ-aminolevulinic acid 0.1~100 ppm per feed 1 kg was added to feed for breeding. This result is identical to the result that δ-aminolevulinic acid has shown no toxic effects on fish cell line.

TABLE 5

Breeding Results of Bastardhalibut and *Sebastes schlegeli* according to δ-aminolevulinic acid treatment

| δ-aminolevulinic acid administration method | Fish species | Fish number | Mortality during Cultivation | Viability (%) |
|---|---|---|---|---|
| Administration to fish tanks | Bastardhalibut | 20 | 0 | 100 |
| | *Sebastes schlegeli* | 20 | 0 | 100 |
| Oral Administration | Bastardhalibut | 20 | 0 | 100 |
| | *Sebastes schlegeli* | 20 | 0 | 100 |
| Non-administration control | Bastardhalibut | 20 | 0 | 100 |
| | *Sebastes schlegeli* | 20 | 0 | 100 |

Experiment 2: Prevention Effect for Infection by Marine Pathogenic Bacteria, *Edwardsiella tarda*

As the same method of above Experiment 1, fishes of both control group and experiment group were prepared and artificially infected by direct abdominal injection of *Edwardsiella tarda* $10^5$ CFU per 1 fish. Each experimental fish was moved to fish tanks for monitoring and monitored for mortality according to infection for 2 weeks and viability after 2 weeks. As shown in Table 6, non-administered group without δ-aminolevulinic acid administration has shown viability of 5~10%, while treated group with δ-aminolevulinic acid by digestion method and oral administration method has shown much higher viability.

TABLE 6

Prevention Effect for Artificial Infection by *Edwardsiella tarda* of δ-aminolevulinic acid-treated Bastardhalibut and *Sebastes schlegeli*

| Administration method | Conc. of δ-aminolevulinic acid | Fish species | Fish number | Mortality during Cultivation | Viability (%) |
|---|---|---|---|---|---|
| Administration to fish tanks | 10 ppm | Bastardhalibut | 20 | 2 | 90 |
| | 10 ppm | *Sebastes schlegeli* | 20 | 3 | 85 |
| | 1.0 ppm | Bastardhalibut | 20 | 3 | 85 |
| | 1.0 ppm | *Sebastes schlegeli* | 20 | 2 | 90 |
| | 0.1 ppm | Bastardhalibut | 20 | 5 | 75 |
| | 0.1 ppm | *Sebastes schlegeli* | 20 | 5 | 75 |
| | 0.01 ppm | Bastardhalibut | 20 | 7 | 65 |
| | 0.01 ppm | *Sebastes schlegeli* | 20 | 7 | 65 |
| Administration orally | 100 ppm | Bastardhalibut | 20 | 1 | 95 |
| | 100 ppm | *Sebastes schlegeli* | 20 | 2 | 90 |
| | 10 ppm | Bastardhalibut | 20 | 3 | 85 |
| | 10 ppm | *Sebastes schlegeli* | 20 | 3 | 85 |
| | 1.0 ppm | Bastardhalibut | 20 | 6 | 70 |
| | 1.0 ppm | *Sebastes schlegeli* | 20 | 4 | 80 |
| | 0.01 ppm | Bastardhalibut | 20 | 5 | 75 |
| | 0.01 ppm | *Sebastes schlegeli* | 20 | 6 | 70 |
| Non-administration control | | Bastardhalibut | 20 | 19 | 5 |
| | | *Sebastes schlegeli* | 20 | 18 | 10 |

Experiment 3: Prevention Effect for Infection by Marine Pathogenic Bacteria, *Streptococcus* sp.

Bastardhalibut and *Sebastes schlegeli* were infected by *Streptococcus* sp. by abdominal injection with the same method of fish breeding, δ-aminolevulinic acid treatment and artificial infection carried out in Experiment 1 and 2. Each experimental fish was moved to fish tanks for monitoring and monitored for mortality according to infection for 2 weeks. As shown in Table 7, the non-administered group without δ-aminolevulinic acid administration has shown viability of 5~10%. The treated group, with δ-aminolevulinic acid by tank administration method and oral administration method, has shown viability of higher than 65%. This result is little lower than that of above Experiment 2, according to the attack of *Edwardsiella tarda*, but is still a relatively high viability.

TABLE 7

Prevention Effect for Artificial Infection by Streptococcus sp of δ-aminolevulinic acid-treated Bastardhalibut and *Sebastes schlegeli*

| Administration method | Conc. of δ-aminolevulinic acid | Fish species | Fish number | Mortality during Cultivation | Viability (%) |
|---|---|---|---|---|---|
| Administration to fish tanks | 10 ppm | Bastardhalibut | 20 | 3 | 85 |
| | 10 ppm | *Sebastes schlegeli* | 20 | 4 | 80 |
| | 1.0 ppm | Bastardhalibut | 20 | 5 | 75 |
| | 1.0 ppm | *Sebastes schlegeli* | 20 | 3 | 85 |
| | 0.1 ppm | Bastardhalibut | 20 | 7 | 65 |
| | 0.1 ppm | *Sebastes schlegeli* | 20 | 7 | 65 |
| | 0.01 ppm | Bastardhalibut | 20 | 8 | 60 |
| | 0.01 ppm | *Sebastes schlegeli* | 20 | 8 | 60 |
| Oral Administration | 100 ppm | Bastardhalibut | 20 | 3 | 85 |
| | 100 ppm | *Sebastes schlegeli* | 20 | 2 | 90 |
| | 10 ppm | Bastardhalibut | 20 | 4 | 80 |
| | 10 ppm | *Sebastes schlegeli* | 20 | 3 | 85 |
| | 1.0 ppm | Bastardhalibut | 20 | 7 | 65 |
| | 1.0 ppm | *Sebastes schlegeli* | 20 | 6 | 70 |
| | 0.1 ppm | Bastardhalibut | 20 | 7 | 65 |
| | 0.1 ppm | *Sebastes schlegeli* | 20 | 6 | 70 |
| Non-administration control | | Bastardhalibut | 20 | 19 | 5 |
| | | *Sebastes schlegeli* | 20 | 19 | 5 |

Experiment 4: Prevention Effect for Infection by Marine Pathogenic Bacteria, *Staphylococcus epidermis*.

Bastardhalibut and *Sebastes schlegeli* were infected by fected by *Staphylococcus epidermis* through abdominal injection with the same method of fish breeding; δ-aminolevulinic acid treatment and artificial carried out in Experiment 1 and 2. Each experimental fish was moved to fish tanks for monitoring and monitored for mortality according to infection for 2 weeks. As shown in Table 8, the non-administered group without δ-aminolevulinic acid administration has shown viability of about 5%. The treated group, with δ-aminolevulinic acid by tank administraion method and oral administration method, has shown high viability.

TABLE 8

Prevention Effect for Artificial Infection by *Streptococcus epidermis*. of δ-aminolevulinic acid-treated Bastardhalibut and *Sebastes schlegeli*

| Administration method | Conc. of δ-aminolevulinic acid | Fish species | Fish number | Mortality during Cultivation | Viability (%) |
|---|---|---|---|---|---|
| Administration to fish tanks | 10 ppm | Bastardhalibut | 20 | 5 | 75 |
| | 10 ppm | *Sebastes schlegeli* | 20 | 4 | 80 |
| | 1.0 ppm | Bastardhalibut | 20 | 7 | 65 |
| | 1.0 ppm | *Sebastes schlegeli* | 20 | 4 | 80 |
| | 0.1 ppm | Bastardhalibut | 20 | 7 | 65 |
| | 0.1 ppm | *Sebastes schlegeli* | 20 | 9 | 55 |
| | 0.01 ppm | Bastardhalibut | 20 | 9 | 55 |
| | 0.01 ppm | *Sebastes schlegeli* | 20 | 9 | 55 |
| Oral Administration | 100 ppm | Bastardhalibut | 20 | 4 | 80 |
| | 100 ppm | *Sebastes schlegeli* | 20 | 4 | 80 |
| | 10 ppm | Bastardhalibut | 20 | 6 | 70 |
| | 10 ppm | *Sebastes schlegeli* | 20 | 5 | 75 |
| | 1.0 ppm | Bastardhalibut | 20 | 9 | 55 |
| | 1.0 ppm | *Sebastes schlegeli* | 20 | 10 | 50 |
| | 0.1 ppm | Bastardhalibut | 20 | 10 | 50 |
| | 0.1 ppm | *Sebastes schlegeli* | 20 | 10 | 50 |
| Non-administration control | | Bastardhalibut | 20 | 19 | 5 |
| | | *Sebastes schlegeli* | 20 | 19 | 5 |

Experiment 5: Prevention Effect for Infection by Marine Pathogenic Bacteria, *Staphylococcus* sp.

Bastardhalibut and *Sebastes schlegeli* were infected by *Staphylococcus* sp. by abdominal injection with the same method of fish breeding δ-aminolevulinic acid treatment and artificial infection carried out in Experiment 1 and 2. Each experimental fish was moved to fish tanks for monitoring and monitored for mortality according to infection for 2 weeks. As shown in Table 9, the non-administered group without δ-aminolevulinic acid administration has shown viability of about 5%, while the treated group with δ-aminolevulinic acid by tank administraion method and oral administration method has shown viability of higher than 55%.

TABLE 9

Prevention Effect for Artificial Infection by Streptococcus sp. of δ-aminolevulinic acid-treated Bastardhalibut and *Sebastes schlegeli*

| Administration method | Conc. of δ-aminolevulinic acid | Fish species | Fish number | Mortality during Cultivation | Viability (%) |
|---|---|---|---|---|---|
| Administration to fish tanks | 10 ppm | Bastardhalibut | 20 | 1 | 95 |
| | 10 ppm | *Sebastes schlegeli* | 20 | 2 | 90 |
| | 1.0 ppm | Bastardhalibut | 20 | 2 | 90 |
| | 1.0 ppm | *Sebastes schlegeli* | 20 | 1 | 95 |
| | 0.1 ppm | Bastardhalibut | 20 | 5 | 75 |
| | 0.1 ppm | *Sebastes schlegeli* | 20 | 7 | 65 |
| | 0.01 ppm | Bastardhalibut | 20 | 9 | 55 |
| | 0.01 ppm | *Sebastes schlegeli* | 20 | 8 | 60 |
| Oral Administration | 100 ppm | Bastardhalibut | 20 | 2 | 90 |
| | 100 ppm | *Sebastes schlegeli* | 20 | 2 | 90 |
| | 10 ppm | Bastardhalibut | 20 | 1 | 95 |
| | 10 ppm | *Sebastes schlegeli* | 20 | 2 | 90 |
| | 1.0 ppm | Bastardhalibut | 20 | 7 | 65 |
| | 1.0 ppm | *Sebastes schlegeli* | 20 | 9 | 55 |
| | 0.1 ppm | Bastardhalibut | 20 | 9 | 55 |
| | 0.1 ppm | *Sebastes schlegeli* | 20 | 10 | 50 |

TABLE 9-continued

Prevention Effect for Artificial Infection by Streptococcus sp. of δ-aminolevulinic acid-treated Bastardhalibut and *Sebastes schlegeli*

| Administration method | Conc. of δ-amino-levulinic acid | Fish species | Fish number | Mortality during Cultivation | Viability (%) |
|---|---|---|---|---|---|
| Non-administration control | | Bastardhalibut | 20 | 19 | 5 |
| | | *Sebastes schlegeli* | 20 | 19 | 5 |

Experiment 6: Prevention Effect for Infection by Marine Pathogenic Bacteria, *Pseudomonas* sp.

Bastardhalibut and *Sebastes schlegeli* were infected by *Pseudomonas* sp. through abdominal injection with the same method of fish breeding; δ-aminolevulinic acid treatment and artificial infection carried out in Experiment 1 and 2. Each experimental fish was moved to fish tanks for monitoring and monitored for mortality according to infection for 2 weeks. As shown in Table 10, the non-administered group without δ-aminolevulinic acid administration has shown viability of 5~10%, while the treated group with δ-aminolevulinic acid by tank administraion method and oral administration method has shown much higher viability.

TABLE 10

Prevention Effect for Artificial Infection by Pseudomonas sp. of δ-aminolevulinic acid-treated Bastardhalibut and *Sebastes schlegeli*

| Administration method | Conc. of δ-amino-levulinic acid | Fish species | Fish number | Mortality during Cultivation | Viability (%) |
|---|---|---|---|---|---|
| Administration to fish tanks | 10 ppm | Bastardhalibut | 20 | 2 | 90 |
| | 10 ppm | *Sebastes schlegeli* | 20 | 2 | 90 |
| | 1.0 ppm | Bastardhalibut | 20 | 2 | 90 |
| | 1.0 ppm | *Sebastes schlegeli* | 20 | 3 | 85 |
| | 0.1 ppm | Bastardhalibut | 20 | 6 | 70 |
| | 0.1 ppm | *Sebastes schlegeli* | 20 | 9 | 55 |
| | 0.01 ppm | Bastardhalibut | 20 | 8 | 60 |
| | 0.01 ppm | *Sebastes schlegeli* | 20 | 9 | 55 |
| Oral Administration | 100 ppm | Bastardhalibut | 20 | 2 | 90 |
| | 100 ppm | *Sebastes schlegeli* | 20 | 3 | 85 |
| | 10 ppm | Bastardhalibut | 20 | 2 | 90 |
| | 10 ppm | *Sebastes schlegeli* | 20 | 3 | 85 |
| | 1.0 ppm | Bastardhalibut | 20 | 9 | 55 |
| | 1.0 ppm | *Sebastes schlegeli* | 20 | 8 | 60 |
| | 0.1 ppm | Bastardhalibut | 20 | 8 | 60 |
| | 0.1 ppm | *Sebastes schlegeli* | 20 | 8 | 60 |
| Non-administration control | | Bastardhalibut | 20 | 19 | 5 |
| | | *Sebastes schlegeli* | 20 | 17 | 15 |

Experiment 7: Prevention Effect for Infection by Marine Pathogenic Bacteria, *Vibrio anguillarum.*

Bastardhalibut and *Sebastes schlegeli* were infected by *Vibrio anguillarum* through abdominal injection with the same method of fish breeding; δ-aminolevulinic acid treatment and artificial infection carried out in Experiment 1 and 2. Each experimental fishes were moved to fish tanks for monitoring and monitored for mortality according to infection for 2 weeks. As shown in Table 11, the non-administered group without δ-aminolevulinic acid administration has shown viability of 10~15%. On the other hand, the treated group with δ-aminolevulinic acid by tank administraion method and oral administration method has shown much higher viability.

TABLE 11

Prevention Effect for Artificial Infection by Vibrio anguillarum. of δ-aminolevulinic acid-treated Bastardhalibut and *Sebastes schlegeli*

| Administration method | Conc. of δ-amino-levulinic acid | Fish species | Fish number | Mortality during Cultivation | Viability (%) |
|---|---|---|---|---|---|
| Administration to fish tanks | 10 ppm | Bastardhalibut | 20 | 3 | 85 |
| | 10 ppm | *Sebastes schlegeli* | 20 | 2 | 90 |
| | 1.0 ppm | Bastardhalibut | 20 | 2 | 80 |
| | 1.0 ppm | *Sebastes schlegeli* | 20 | 1 | 85 |
| | 0.1 ppm | Bastardhalibut | 20 | 7 | 65 |
| | 0.1 ppm | *Sebastes schlegeli* | 20 | 8 | 60 |
| | 0.01 ppm | Bastardhalibut | 20 | 7 | 65 |
| | 0.01 ppm | *Sebastes schlegeli* | 20 | 8 | 60 |
| Oral Administration | 100 ppm | Bastardhalibut | 20 | 2 | 90 |
| | 100 ppm | *Sebastes schlegeli* | 20 | 2 | 90 |
| | 10 ppm | Bastardhalibut | 20 | 3 | 85 |
| | 10 ppm | *Sebastes schlegeli* | 20 | 4 | 80 |
| | 1.0 ppm | Bastardhalibut | 20 | 9 | 55 |
| | 1.0 ppm | *Sebastes schlegeli* | 20 | 7 | 65 |
| | 0.1 ppm | Bastardhalibut | 20 | 7 | 65 |
| | 0.1 ppm | *Sebastes schlegeli* | 20 | 8 | 60 |
| Non-administration control | | Bastardhalibut | 20 | 18 | 10 |
| | | *Sebastes schlegeli* | 20 | 17 | 15 |

EXAMPLE 5

Treatment Effect of Pathogenic Bacteria Infected Marine Fry by δ-Aminolevulinic Acid Digestion In Vivo To be used as experimental fish in this example, fry of Bastardhalibut and *Sebastes schlegeli* (mean body weight 2 g), 50 per each breeding tank, were preliminary-bred for 1 week and stabilized. Six species of fish pathogenic bacteria (*Edwardsiella tarda, Streptococcus* sp., *Staphylococcus* sp., *Staphylococcus epidermis, Pseudomonas* sp. and *Vibrio anguillarum*) were used as pathogenic organisms for artificial infection. The artificial infection methods were carried out by the digestion method. Pathogenic organisms were applied into fish tanks and digested in seawater, wherein the concentration of organisms has adjusted to $10^4$ CFU/mL for an hour, and infected. Treatment conditions are as follows. After artificial infection. Infected fishes were moved to fish tanks and kept in the infection period for 3 days. On the fourth day of infection, 0.1, 1.0, 5 and 10 ppm δ-aminolevulinic acid were introduced to use as breeding water. Fish was bred in aerobic condition for 1~24 hours without exchanging water and then, bred for 2 weeks after exchanging with clean seawater. Then, they were monitored to check for the mortality of fish according to infection. In the control groups, after each bacteria were identically introduced through the digestion method, mortality of Bastardhalibut and *Sebastes schlegeli* according to bacteria infection was identified while breeding with non-treated condition of δ-aminolevulinic acid. As a result of this experiment, δ-aminolevulinic acid-treated groups have shown high viability in both Bastardhalibut (Table 12~Table 15) and *Sebastes schlegeli* (Table 16~Table 19).

TABLE 12

Treatment Effect for Bastardhalibu Infected by Pathogenic Bacteria according to 0.1 ppm δ-Aminolevulinic Acid Treatment

| Pathogenic Bacteria | | Fish number | Viability(%) |
|---|---|---|---|
| *Edwardsiella tarda* | Treated Group | 50 | 54 |
| | Control Group | 50 | 4 |
| Streptococcus sp. | Treated Group | 50 | 46 |
| | Control Group | 50 | 14 |
| *Staphylococcus epidermis* | Treated Group | 50 | 42 |
| | Control Group | 50 | 36 |
| Staphylococcus sp. | Treated Group | 50 | 54 |
| | Control Group | 50 | 6 |
| Pseudomonas sp. | Treated Group | 50 | 50 |
| | Control Group | 50 | 16 |
| *Vibrio anguillarum* | Treated Group | 50 | 56 |
| | Control Group | 50 | 40 |

TABLE 13

Treatment Effect for Bastardhalibu Infected by Pathogenic Bacteria according to 1.0 ppm δ-Aminolevulinic Acid Treatment

| Pathogenic Bacteria | | Fish number | Viability(%) |
|---|---|---|---|
| *Edwardsiella tarda* | Treated Group | 50 | 76 |
| | Control Group | 50 | 4 |
| Streptococcus sp. | Treated Group | 50 | 64 |
| | Control Group | 50 | 14 |
| *Staphylococcus epidermis* | Treated Group | 50 | 66 |
| | Control Group | 50 | 36 |
| Staphylococcus sp. | Treated Group | 50 | 66 |
| | Control Group | 50 | 6 |
| Pseudomonas sp. | Treated Group | 50 | 70 |
| | Control Group | 50 | 16 |
| *Vibrio anguillarum* | Treated Group | 50 | 66 |
| | Control Group | 50 | 40 |

TABLE 14

Treatment Effect for Bastardhalibu Infected by Pathogenic Bacteria according to 5.0 ppm δ-Aminolevulinic Acid Treatment

| Pathogenic Bacteria | | Fish number | Viability(%) |
|---|---|---|---|
| *Edwardsiella tarda* | Treated Group | 50 | 86 |
| | Control Group | 50 | 4 |
| Streptococcus sp. | Treated Group | 50 | 84 |
| | Control Group | 50 | 14 |
| *Staphylococcus epidermis* | Treated Group | 50 | 80 |
| | Control Group | 50 | 36 |
| Staphylococcus sp. | Treated Group | 50 | 84 |
| | Control Group | 50 | 6 |
| Pseudomonas sp. | Treated Group | 50 | 80 |
| | Control Group | 50 | 16 |
| *Vibrio anguillarum* | Treated Group | 50 | 84 |
| | Control Group | 50 | 40 |

TABLE 15

Treatment Effect for Bastardhalibu Infected by Pathogenic Bacteria according to 10 ppm δ-Aminolevulinic Acid Treatment

| Pathogenic Bacteria | | Fish number | Viability(%) |
|---|---|---|---|
| *Edwardsiella tarda* | Treated Group | 50 | 84 |
| | Control Group | 50 | 4 |
| Streptococcus sp. | Treated Group | 50 | 90 |
| | Control Group | 50 | 14 |
| *Staphylococcus epidermis* | Treated Group | 50 | 84 |
| | Control Group | 50 | 36 |
| Staphylococcus sp. | Treated Group | 50 | 84 |
| | Control Group | 50 | 6 |
| Pseudomonas sp. | Treated Group | 50 | 84 |
| | Control Group | 50 | 16 |
| *Vibrio anguillarum* | Treated Group | 50 | 80 |
| | Control Group | 50 | 40 |

TABLE 16

Treatment Effect for *Sebastes schlegeli* Infected by Pathogenic Bacteria according to 0.1 ppm δ-Aminolevulinic Acid Treatment

| Pathogenic Bacteria | | Fish number | Viability(%) |
|---|---|---|---|
| *Edwardsiella tarda* | Treated Group | 50 | 60 |
| | Control Group | 50 | 10 |
| Streptococcus sp. | Treated Group | 50 | 50 |
| | Control Group | 50 | 24 |
| *Staphylococcus epidermis* | Treated Group | 50 | 40 |
| | Control Group | 50 | 16 |
| Staphylococcus sp. | Treated Group | 50 | 50 |
| | Control Group | 50 | 14 |
| Pseudomonas sp. | Treated Group | 50 | 40 |
| | Control Group | 50 | 20 |
| *Vibrio anguillarum* | Treated Group | 50 | 50 |
| | Control Group | 50 | 20 |

TABLE 17

Treatment Effect for *Sebastes schlegeli* Infected by Pathogenic Bacteria according to 1.0 ppm δ-Aminolevulinic Acid Treatment

| Pathogenic Bacteria | | Fish number | Viability(%) |
|---|---|---|---|
| *Edwardsiella tarda* | Treated Group | 50 | 80 |
| | Control Group | 50 | 10 |
| Streptococcus sp. | Treated Group | 50 | 76 |
| | Control Group | 50 | 24 |
| *Staphylococcus epidermis* | Treated Group | 50 | 70 |
| | Control Group | 50 | 16 |
| Staphylococcus sp. | Treated Group | 50 | 76 |
| | Control Group | 50 | 14 |
| Pseudomonas sp. | Treated Group | 50 | 76 |
| | Control Group | 50 | 20 |
| *Vibrio anguillarum* | Treated Group | 50 | 74 |
| | Control Group | 50 | 20 |

TABLE 18

Treatment Effect for *Sebastes schlegeli* Infected by Pathogenic Bacteria according to 5.0 ppm δ-Aminolevulinic Acid Treatment

| Pathogenic Bacteria | | Fish number | Viability(%) |
|---|---|---|---|
| *Edwardsiella tarda* | Treated Group | 50 | 84 |
| | Control Group | 50 | 10 |
| Streptococcus sp. | Treated Group | 50 | 86 |
| | Control Group | 50 | 24 |
| *Staphylococcus epidermis* | Treated Group | 50 | 66 |
| | Control Group | 50 | 16 |

TABLE 18-continued

Treatment Effect for *Sebastes schlegeli* Infected by Pathogenic Bacteria according to 5.0 ppm δ-Aminolevulinic Acid Treatment

| Pathogenic Bacteria | | Fish number | Viability(%) |
|---|---|---|---|
| Staphylococcus sp. | Treated Group | 50 | 84 |
| | Control Group | 50 | 14 |
| Pseudomonas sp. | Treated Group | 50 | 86 |
| | Control Group | 50 | 20 |
| *Vibrio anguillarum* | Treated Group | 50 | 84 |
| | Control Group | 50 | 20 |

TABLE 19

Treatment Effect for *Sebastes schlegeli* Infected by Pathogenic Bacteria according to 10 ppm δ-Aminolevulinic Acid Treatment

| Pathogenic Bacteria | | Fish number | Viability(%) |
|---|---|---|---|
| *Edwardsiella tarda* | Treated Group | 50 | 94 |
| | Control Group | 50 | 10 |
| Streptococcus sp. | Treated Group | 50 | 86 |
| | Control Group | 50 | 24 |
| *Staphylococcus epidermis* | Treated Group | 50 | 84 |
| | Control Group | 50 | 16 |
| Staphylococcus sp. | Treated Group | 50 | 86 |
| | Control Group | 50 | 14 |
| Pseudomonas sp. | Treated Group | 50 | 84 |
| | Control Group | 50 | 20 |
| *Vibrio anguillarum* | Treated Group | 50 | 86 |
| | Control Group | 50 | 20 |

EXAMPLE 6

Treatment Effect of Pathogenic Bacteria Infected Fishes by Oral Administration of δ-Aminolevulinic Acid In this example, fry of Bastardhalibut and *Sebastes schlegeli* (mean body weight 2 g), 50 per each breeding tank, were preliminary-bred for 1 week and stabilized. Six species of fish pathogenic bacteria, *Edwardsiella tarda, Streptococcus* sp., *Staphylococcus* sp., *Staphylococcus epidermis, Pseudomonas* sp. and *Vibrio anguillarum* were used as pathogenic organisms for artificial infection. The artificial infection methods were carried out through the digestion method. Pathogenic organisms were applied into fish tanks and introduced into seawater for an hour, wherein the concentration of organisms adjusted to $10^4$ CFU/mL. Treatment conditions are as follows; after artificial infection, infected fish were moved to fish tanks and kept in the infection period for 3 days. On the fourth day of infection, 0.1~50 ppm of δ-aminolevulinic acid for feed were added. The fish were bred for 2 weeks after exchanging with clean seawater and the mortality of fish according to infection was monitored. In the control groups, after each bacteria were identically infected through digestion method, mortality of Bastardhalibut and *Sebastes schlegeli* according to bacteria infection was identified while breeding with marketing assorted feed without δ-aminolevulinic acid. As a result of this experiment, δ-aminolevulinic acid-treated groups have shown high viability in both Bastardhalibut (Table 20~Table 23) and *Sebastes schlegeli* (Table 24~Table 27).

TABLE 20

Treatment Effect for Bastardhalibut Infected by Pathogenic Bacteria according to 0.1 ppm δ-Aminolevulinic Acid Treatment

| Pathogenic Bacteria | | Fish number | Viability(%) |
|---|---|---|---|
| *Edwardsiella tarda* | Treated Group | 50 | 42 |
| | Control Group | 50 | 4 |
| Streptococcus sp. | Treated Group | 50 | 36 |
| | Control Group | 50 | 10 |
| *Staphylococcus epidermis* | Treated Group | 50 | 42 |
| | Control Group | 50 | 30 |
| Staphylococcus sp. | Treated Group | 50 | 42 |
| | Control Group | 50 | 8 |
| Pseudomonas sp. | Treated Group | 50 | 42 |
| | Control Group | 50 | 14 |
| *Vibrio anguillarum* | Treated Group | 50 | 44 |
| | Control Group | 50 | 32 |

TABLE 21

Treatment Effect for Bastardhalibut Infected by Pathogenic Bacteria according to 1.0 ppm δ-Aminolevulinic Acid Treatment

| Pathogenic Bacteria | | Fish number | Viability (%) |
|---|---|---|---|
| *Edwardsiella tarda* | Treated Group | 50 | 68 |
| | Control Group | 50 | 4 |
| Streptococcus sp. | Treated Group | 50 | 74 |
| | Control Group | 50 | 10 |
| *Staphylococcus epidermis* | Treated Group | 50 | 68 |
| | Control Group | 50 | 30 |
| Staphylococcus sp. | Treated Group | 50 | 72 |
| | Control Group | 50 | 8 |
| Pseudomonas sp. | Treated Group | 50 | 68 |
| | Control Group | 50 | 14 |
| *Vibrio anguillarum* | Treated Group | 50 | 72 |
| | Control Group | 50 | 32 |

TABLE 22

Treatment Effect for Bastardhalibut Infected by Pathogenic Bacteria according to 100 ppm δ-Aminolevulinic Acid Treatment

| Pathogenic Bacteria | | Fish number | Viability (%) |
|---|---|---|---|
| *Edwardsiella tarda* | Treated Group | 50 | 82 |
| | Control Group | 50 | 4 |
| Streptococcus sp. | Treated Group | 50 | 86 |
| | Control Group | 50 | 10 |
| *Staphylococcus epidermis* | Treated Group | 50 | 86 |
| | Control Group | 50 | 30 |
| Staphylococcus sp. | Treated Group | 50 | 86 |
| | Control Group | 50 | 8 |
| Pseudomonas sp. | Treated Group | 50 | 82 |
| | Control Group | 50 | 14 |
| *Vibrio anguillarum* | Treated Group | 50 | 88 |
| | Control Group | 50 | 32 |

TABLE 23

Treatment Effect for Bastardhalibut Infected by Pathogenic Bacteria according to 50 ppm δ-Aminolevulinic Acid Treatment

| Pathogenic Bacteria | | Fish number | Viability (%) |
|---|---|---|---|
| *Edwardsiella tarda* | Treated Group | 50 | 92 |
| | Control Group | 50 | 4 |
| Streptococcus sp. | Treated Group | 50 | 90 |
| | Control Group | 50 | 10 |
| *Staphylococcus epidermis* | Treated Group | 50 | 94 |
| | Control Group | 50 | 30 |

TABLE 23-continued

Treatment Effect for Bastardhalibut Infected by Pathogenic Bacteria according to 50 ppm δ-Aminolevulinic Acid Treatment

| Pathogenic Bacteria | | Fish number | Viability (%) |
|---|---|---|---|
| Staphylococcus sp. | Treated Group | 50 | 92 |
| | Control Group | 50 | 8 |
| Pseudomonas sp. | Treated Group | 50 | 88 |
| | Control Group | 50 | 14 |
| Vibrio anguillarum | Treated Group | 50 | 90 |
| | Control Group | 50 | 32 |

TABLE 24

Treatment Effect for Bastardhalibut Infected by Pathogenic Bacteria according to 0.1 ppm δ-Aminolevulinic Acid Treatment

| Pathogenic Bacteria | | Fish number | Viability (%) |
|---|---|---|---|
| Edwardsiella tarda | Treated Group | 50 | 52 |
| | Control Group | 50 | 8 |
| Streptococcus sp. | Treated Group | 50 | 44 |
| | Control Group | 50 | 18 |
| Staphylococcus epidermis | Treated Group | 50 | 36 |
| | Control Group | 50 | 28 |
| Staphylococcus sp. | Treated Group | 50 | 48 |
| | Control Group | 50 | 12 |
| Pseudomonas sp. | Treated Group | 50 | 52 |
| | Control Group | 50 | 12 |
| Vibrio anguillarum | Treated Group | 50 | 50 |
| | Control Group | 50 | 28 |

TABLE 25

Treatment Effect for Bastardhalibut Infected by Pathogenic Bacteria according to 1.0 ppm δ-Aminolevulinic Acid Treatment

| Pathogenic Bacteria | | Fish number | Viability (%) |
|---|---|---|---|
| Edwardsiella tarda | Treated Group | 50 | 62 |
| | Control Group | 50 | 8 |
| Streptococcus sp. | Treated Group | 50 | 66 |
| | Control Group | 50 | 18 |
| Staphylococcus epidermis | Treated Group | 50 | 63 |
| | Control Group | 50 | 28 |
| Staphylococcus sp. | Treated Group | 50 | 70 |
| | Control Group | 50 | 12 |
| Pseudomonas sp. | Treated Group | 50 | 78 |
| | Control Group | 50 | 12 |
| Vibrio anguillarum | Treated Group | 50 | 74 |
| | Control Group | 50 | 28 |

TABLE 26

Treatment Effect for Bastardhalibut Infected by Pathogenic Bacteria according to 10 ppm δ-Aminolevulinic Acid Treatment

| Pathogenic Bacteria | | Fish number | Viability (%) |
|---|---|---|---|
| Edwardsiella tarda | Treated Group | 50 | 68 |
| | Control Group | 50 | 8 |
| Streptococcus sp. | Treated Group | 50 | 72 |
| | Control Group | 50 | 18 |
| Staphylococcus epidermis | Treated Group | 50 | 64 |
| | Control Group | 50 | 28 |
| Staphylococcus sp. | Treated Group | 50 | 78 |
| | Control Group | 50 | 12 |
| Pseudomonas sp. | Treated Group | 50 | 86 |
| | Control Group | 50 | 12 |
| Vibrio anguillarum | Treated Group | 50 | 84 |
| | Control Group | 50 | 28 |

TABLE 27

Treatment Effect for Bastardhalibut Infected by Pathogenic Bacteria according to 50 ppm δ-Aminolevulinic Acid Treatment

| Pathogenic Bacteria | | Fish number | Viability (%) |
|---|---|---|---|
| Edwardsiella tarda | Treated Group | 50 | 88 |
| | Control Group | 50 | 8 |
| Streptococcus sp. | Treated Group | 50 | 82 |
| | Control Group | 50 | 18 |
| Staphylococcus epidermis | Treated Group | 50 | 86 |
| | Control Group | 50 | 28 |
| Staphylococcus sp. | Treated Group | 50 | 88 |
| | Control Group | 50 | 12 |
| Pseudomonas sp. | Treated Group | 50 | 84 |
| | Control Group | 50 | 12 |
| Vibrio anguillarum | Treated Group | 50 | 86 |
| | Control Group | 50 | 28 |

EXAMPLE 7

Treatment Effect of Virus-Infected Fish

In this present example, as carried out in Experiment 2 of Example 3, from the result that inhibition effect of virus infection in vitro by δ-aminolevulinic acid treatment was ascertained, fish whose diseases were in progress by virus infection, decrease in the mortality of infected fish body was ascertained when treated with δ-aminolevulinic acid. *Pagrus major* diagnosed by the PCR method among a school of Iridovirus-infected fish from a fish farm nearby Yeosu, 30 of each were separated and contained in 3 fish tanks. They were divided to group A, B, C and control group. Temporary changes in mortality was ascertained in 10 ppm δ-aminolevulinic acid-treated A group, 1.0 ppm δ-aminolevulinic acid-treated B group, 0.1 ppm δ-aminolevulinic acid-treated C group and untreated control group by using δ-aminolevulinic acid produced by the inventor. Each δ-aminolevulinic acid-treated group was treated 3 times in 3 week intervals and 10 days results were reported. In the case of actual fish farms, the mortality by virus infection reaches up to 70%. However, as shown in the result of infected fish of Table 28, in the present experimental condition, cumulative mortality of infected fish without treatment has reached up to 50% until 10$^{th}$ day of experimental period. In δ-aminolevulinic acid-treated groups, low mortalities of 17%, 17% and 27% was shown in the condition of A, B and C groups during 10 days, respectively. From these results, δ-aminolevulinic acid has shown treatment effects on virus disease and the viability of infected fish was increased with δ-aminolevulinic acid treatment.

TABLE 28

Viability change of infected Pagrus major by Iridovirus according to δ-Aminolevulinic Acid Treatment

| Conc. of δ-aminolevulinic acid | Viable Fish number According to Elapsed days After Treatment | | | | | | | | | | |
|---|---|---|---|---|---|---|---|---|---|---|---|
| | 0 | 1 | 2 | 3 | 4 | 5 | 6 | 7 | 8 | 9 | 10 |
| 10 ppm | 30 | 28 | 26 | 26 | 26 | 26 | 26 | 25 | 25 | 25 | 25 |
| 1.0 ppm | 30 | 28 | 26 | 26 | 26 | 25 | 25 | 25 | 25 | 25 | 25 |
| 0.1 ppm | 30 | 25 | 25 | 23 | 23 | 23 | 22 | 22 | 22 | 22 | 22 |
| 0 ppm | 30 | 23 | 22 | 19 | 17 | 17 | 17 | 16 | 16 | 16 | 16 |

EXAMPLE 8

Treatment of *Edwardsiella* bacteria-Infected Fish

Infected fish cultivated in the terrestrial fish tank were found in a fish farm, where flatfish (mean weight 11 g) were dying by spontaneous attack. The main source of infection was *Edwardsiella tarda*. About 30~40% of cumulative mortality per cultivating tank has shown after 5 days since the mortality started. Even when δ-aminolevulinic acid was treated, it was discovered that some fishes showed lesion such as abdominal inflation, and hernia of the anus by *Edwardsiella tarda* infection. This indicated that the disease has been in serious progress and δ-aminolevulinic acid was added to cultivating tank. On the first day, 0.1 ppm δ-aminolevulinic acid was digestion-treated in two tanks for 2 hrs and on the second and third day, 0.01 ppm δ-aminolevulinic acid was digested for 2 hrs. They were then observed, during the water was exchanged. δ-aminolevulinic acid digestion-treated tanks (about 3,000 fish) has maintained 40% cumulative mortality for 1 week after treatment, while δ-aminolevulinic acid non-treated tanks has shown 60% cumulative mortality and progressive disease was observed, more reporting 20% cumulative mortality thereafter. As a result of this experiment, non-treated groups have shown 80% cumulative mortality, while δ-aminolevulinic acid digestion-treated groups in progressive disease have shown about 40% cumulative mortality and showed distinguished condition in health comparisons.

EXAMPLE 9

Inhibition Effect of δ-aminolevulinic Acid for Fish Pathogenic Scutica

Experiment 1: Extinction Effect for Scutica in vitro

Scutica used in this experiment was taken from epidermal mucus of infected flatfish and suspended in HBSS. The suspension was kept at room temperature for 30 min and centrifuged at 800 rpm for 10 min. The supernatant was removed. The pellet was suspended in MEM-10 (minimum essential medium, 10% FBS, streptomycine, penicilin) and kept for 30 min, and then centrifuged in the same manner as above. The supernatant was removed and left imagoes was gained and made into imagoes suspension with certain number of imagoes by counting with the blood counting machine. The imagoes suspension was subcultured in vitro and inoculated to prepared FHM cell of certain number ($2.5 \times 10^5$ cells/mL) and then cultured at 17° C. Before carrying out the experiment, by measuring the extinction effect for Scutica according to the concentration of δ-aminolevulinic acid and reaction time, optimum δ-aminolevulinic acid concentration and treatment time was examined for Scutica extermination. The Scutica culture solution cultured in FHM cell line was centrifuged at 3000 rpm for 5 min. The supernatant was removed and was added to PBS. It was washed 3 times to use for the experiment. 1.0 M δ-aminolevulinic acid solution made from sterilized $3^{rd}$ distilled water was diluted by 2-fold up to 1000-fold (1.0 mM). Scutica was added to each well of 96-well microplate at an amount of 50 μL. Then, δ-aminolevulinic acid solution diluted by 2 steps were added and cultured for 120 min while the viability of Scutica was monitored. During the culture for 120 min, extinction time was measured in 10 min intervals, at each concentration. Between each inoculation, they were stirred for 5 min and were kept for 5 min. after reaction, 1% trypan blue which is staining solution for organism was added to each wells at an amount of 100 μL and mixed. In cultured Scutica with the diluted solution of δ-aminolevulinic acid, the number of parasites was counted by the blood counting machine, according to time. From the results, as shown in Table 29, at the concentration 500 to 60 mM of δ-aminolevulinic acid, they were completely extinct after 10 min treatment and in the range of 30~15 mM concentration, it took 20 min to extinct Scutica completely and 60 min at the actual concentration of 8 mM. Through the 60 min-treatment, more than 50% of Scutica were extinct. At the actual concentration of 2 mM, about 50% of Scutica was extinct through 1 hour-treatment. At the actual concentration of 500 mM to 2 mM, the fact that more than 90% of Scutica was extinct by treatment of at minimum 2 hours, showed the extermination effect of δ-aminolevulinic acid.

TABLE 29

Viability (%) of Scutica according to δ-Aminolevulinic Acid Treatment Concentration and Reaction Time

| Conc. of δ-aminolevulinic acid | Viable Fish number According to Elapsed days After Treatment | | | | | | | | | | |
|---|---|---|---|---|---|---|---|---|---|---|---|
| | 10 | 20 | 30 | 40 | 50 | 60 | 70 | 80 | 90 | 110 | 120 |
| 500 mM | 0 | 0 | 0 | 0 | 0 | 0 | 0 | 0 | 0 | 0 | 0 |
| 250 mM | 0 | 0 | 0 | 0 | 0 | 0 | 0 | 0 | 0 | 0 | 0 |
| 125 mM | 0 | 0 | 0 | 0 | 0 | 0 | 0 | 0 | 0 | 0 | 0 |
| 60 mM | 0 | 0 | 0 | 0 | 0 | 0 | 0 | 0 | 0 | 0 | 0 |
| 30 mM | 20 | 0 | 0 | 0 | 0 | 0 | 0 | 0 | 0 | 0 | 0 |
| 15 mM | 30 | 0 | 0 | 0 | 0 | 0 | 0 | 0 | 0 | 0 | 0 |
| 8.0 mM | 45 | 50 | 45 | 25 | 40 | 40 | 0 | 0 | 0 | 0 | 0 |
| 4.0 mM | 50 | 50 | 30 | 30 | 20 | 45 | 30 | 45 | 40 | 10 | 10 |
| 2.0 mM | 50 | 60 | 40 | 45 | 35 | 55 | 40 | 40 | 35 | 40 | 10 |

Experiment 2: Prevention Effect for Scutica Artificial Infection of Fish body in vivo 20 flatfish of about 25 g were set into 2 groups and 1 control group and cultivated in circulatory filtering system. In group 1, they were cultivated for 1~3 weeks, maintaining the concentration of δ-aminolevulinic acid at 0.01~50 ppm by administering δ-aminolevulinic acid once every 3 days to the cultivating water. In group 2, they were cultivated for 1~3 weeks by administering δ-aminolevulinic acid solution, which was nebulized at the concentration of 0.1~100 ppm and for artificial assorted feed (EP, fish body weight 3%: 15 g) 1 kg, and dried. In group 1 and the non-treated group, artificial assorted feed on the market with the same amount of feed of group 2 was used without δ-aminolevulinic acid treatment. Artificial infection was carried out by using Scutica imagoes, which were pure-cultured in FHM cell. Artificial infection of imagoes was carried out after 3 weeks and artificial attack method was carried out by directly digesting in culture imago-solution (1000/m) and exposing for 30 min in aeration condition. After artificial infection, experimental fish in each group were transferred to water tanks for monitoring and, the infection and the mortality was observed according to infection for 2 weeks. The water temperature was maintained at 20° C. (±2° C.) throughout the experiment. As shown in Table 30, there was no mortality shown in both group 1, whose δ-aminolevulinic acid concentration was maintained at 10 ppm during breeding and group 2, where δ-aminolevulinic acid 100 ppm per feed 1 kg was added to feed for cultivation without δ-aminolevulinic acid. This result is identical to the result that δ-aminolevulinic acid has shown no toxic effects on fish cell line. Also, Scutica-infected fish by artificial attack, were transferred to water tanks for monitoring and, the mortality was observed according to infection for 2 weeks. Table 31 shows the viability after 2 weeks. As shown in Table 31, the non-treated group without δ-aminolevulinic acid has shown viability of 40~45%, while the treated group, with δ-aminolevulinic acid by digestion method and oral administration method, has shown much higher viability.

TABLE 30

Breeding Results of Bastardhalibut and Sebastes schlegeli according to δ-aminolevulinic acid treatment

| δ-aminolevulinic acid administration method | Fish Species | Fish number | Mortality during Cultivation | Viability (%) |
|---|---|---|---|---|
| Administration to fish tanks | Bastardhalibut | 20 | 0 | 100 |
|  | Sebastes schlegeli | 20 | 0 | 100 |

TABLE 30-continued

Breeding Results of Bastardhalibut and Sebastes schlegeli according to δ-aminolevulinic acid treatment

| δ-aminolevulinic acid adminstration method | Fish Species | Fish number | Mortality during Cultivation | Viability (%) |
|---|---|---|---|---|
| Oral Administration | Bastardhalibut | 20 | 0 | 100 |
|  | Sebastes schlegeli | 20 | 0 | 100 |
| Non-administration control | Bastardhalibut | 20 | 0 | 100 |
|  | Sebastes schlegeli | 20 | 0 | 100 |

TABLE 31

Prevention Effect for Artificial Infection by Scutica of δ-aminolevulinic acid-treated Bastardhalibut and Sebastes schlegeli

| Administration method | Conc. of δ-aminolevulinic acid | Fish species | Fish number | Mortality during Cultivation | Viablity (%) |
|---|---|---|---|---|---|
| Administration to fish tanks | 50 ppm | Bastardhalibut | 20 | 4 | 80 |
|  | 50 ppm | Sebastes schlegeli | 20 | 4 | 80 |
|  | 10 ppm | Bastardhalibut | 20 | 3 | 85 |
|  | 10 ppm | Sebastes schlegeli | 20 | 3 | 85 |
|  | 5.0 ppm | Bastardhalibut | 20 | 3 | 85 |
|  | 5.0 ppm | Sebastes schlegeli | 20 | 3 | 85 |
|  | 1.0 ppm | Bastardhalibut | 20 | 5 | 75 |
|  | 1.0 ppm | Sebastes schlegeli | 20 | 6 | 70 |
|  | 0.1 pm | Bastardhalibut | 20 | 7 | 75 |
|  | 0.1 pm | Sebastes schlegeli | 20 | 8 | 60 |
|  | 0.01 ppm | Bastardhalibut | 20 | 8 | 60 |
|  | 0.01 ppm | Sebastes schlegeli | 20 | 8 | 60 |
| Oral Adminstration | 100 ppm | Bastardhalibut | 20 | 2 | 90 |
|  | 100 ppm | Sebastes schlegeli | 20 | 1 | 95 |
|  | 50 ppm | Bastardhalibut | 20 | 1 | 95 |
|  | 50 ppm | Sebastes schlegeli | 20 | 1 | 95 |
|  | 10 ppm | Bastardhalibut | 20 | 1 | 95 |
|  | 10 ppm | Sebastes schlegeli | 20 | 1 | 95 |
|  | 5 ppm | Bastardhalibut | 20 | 3 | 85 |
|  | 5 ppm | Sebastes schlegeli | 20 | 3 | 85 |
|  | 1.0 ppm | Bastardhalibut | 20 | 6 | 70 |
|  | 1.0 ppm | Sebastes schlegeli | 20 | 5 | 75 |
|  | 0.1 ppm | Bastardhalibut | 20 | 6 | 70 |
|  | 0.1 ppm | Sebastes schlegeli | 20 | 7 | 65 |
| Non-administration control |  | Bastardhalibut | 20 | 11 | 45 |
|  |  | Sebastes schlegeli | 20 | 12 | 40 |

Experiment 3: Application to Scutica-Infected Seedling Nursery

Seedling was produced in flatfish seedling nursery and flatfish fry in seedling nursery, where marketing had stopped due to the infection of Scutica in a marketing stage (the length 5~6 cm). They were treated with δ-aminolevulinic acid made by the inventors. Seriously infected fish were collected from seedling nursery and contained in water tanks and treated. On the first day, the fish were treated with 30 ppm formalin and, on the second and third day, were treated δ-aminolevulinic acid at concentration of 1 ppm for 2 hrs. They were observed with changing waters. Vitality of treated fish was highly improved after 1 day of treatment and continuing mortality had a tendency to remarkably diminish. Cultivation in a water tank of a fish farm where the ozone treatment system, which can control pathogenic organisms in seawater for cultivating, was applied has shown possibility of normal cultivation. After 2 weeks of cultivation, results of the examination of infection through sampling of fish body have shown no infection by Scutica.

EXAMPLE 10

Efficacy of δ-aminolevulinic Acid (ALA) on WSSV Disease of Shrimp

Experiment 1: Prevention for the White Spot Syndrome Virus (WSSV) Infected Shrimp.

The Shrimps (*Penaeus Chinesis*, size 6~8 cm) were immersed in 0.01~10 ppm of EnviroVax for 1.5 hr during 3 days and injected viral homogenate at 4 day.

The Viral homogenate was prepared as follows:
Homogenize 1 g of tissue (gill and stomach) in 1 ml PBS.
Centrifuge at 2,000 rpm for 10 min. at 4° C.
Filter the supernatant by using the 0.45 μm membrane filter.
Dilute the filtrate (1 part of filtrate to 10 parts of PBS).

As shown in Table 32, cumulative mortality after injection, intramuscularly, of 0.1% v/w of body weight for 3 weeks was presented 8% and 6% at 1.0 ppm and 10 ppm respectively.

TABLE 32

| Prevention effect of shrimp infected with WSSV | | | | | | | | | |
|---|---|---|---|---|---|---|---|---|---|
| Concentration | No. of shrimp | Mortality after injection for 3 weeks | | | | | | | Cumulative mortality |
| Control (0 ppm) | 50 | 1 | 2 | 3 | 4 | 5 | 6 | 7 | 21 |
| 0.01 ppm | 50 | 0 | 0 | 15 | 20 | 12 | 3 | — | — | 100% |
| 0.1 ppm | 50 | 0 | 0 | 2 | 3 | 1 | 0 | 0 | 0 | 12% |
| 1.0 ppm | 50 | 0 | 1 | 2 | 1 | 0 | 0 | 0 | 0 | 8% |
| 10 ppm | 50 | 0 | 0 | 3 | 0 | 0 | 0 | 0 | 0 | 6% |

Experiment 2: Treatment for WSSV Infected Shrimp

In this experiment, after injection of the viral homogenate aforementioned in EXPERIMENT 1, treatment group was immersed respectively in 0.01~10 ppm of ALA for 1.5 hour for 3 days.

The experimental result was shown in Table 33. As shown in Table 33, cumulative mortality after injection, imtramuscularly, of 0.1% v/w of body weight for 3 weeks was presented 10% and 8% at 1.0 ppm and 10 ppm respectively.

TABLE 33

| Prevention effect of shrimp infected with WSSV | | | | | | | | | |
|---|---|---|---|---|---|---|---|---|---|
| Concentration | No. of shrimp | Mortality after injection for 3 weeks | | | | | | | Cumulative mortality |
| Control (0 ppm) | 50 | 1 | 2 | 3 | 4 | 5 | 6 | 7 | 21 |
| 0.01 ppm | 50 | 0 | 0 | 15 | 20 | 12 | 3 | — | — | 100% |
| 0.1 ppm | 50 | 0 | 0 | 4 | 3 | 2 | 0 | 0 | 0 | 18% |
| 1.0 ppm | 50 | 0 | 0 | 3 | 2 | 0 | 0 | 0 | 0 | 10% |
| 10 ppm | 50 | 0 | 0 | 3 | 1 | 0 | 0 | 0 | 0 | 8% |

From these results, ALA has shown prevention effects and treatment effects on the shrimp infected with WSSV at the concentration of 0.1~10 ppm.

Inventors carried out actual field test at the Suncheon Shrimp Farm, Chunnam, Korea in the period of May 20, 2000~Oct. 10, 2000. The treated group of ALA at the concentration range of 0.1~10 ppm by feed additive administration method has shown of 70~80% higher yield in harvest.

EXAMPLE 11

Treatment Effect on Eel Disease of Birnavirus

In the example, the experiment was carried out in the field at the Eel Aguacultural Farm, Gochang and Kunsan, in Chunbuk, Korea. Eels were dead by infection of Birnavirus, which was easely confirmed by microscopical or electron microscopical observation.

ALA, at the concentration range of 0.1~10 ppm was added to the farm for 3 months. After 3 weeks administration, motality was decreased to less than 10% (1~2 kg).

What is claimed is:

1. A method for treating fish infected by irido virus comprising adding a composition containing δ-aminolevulinic acid at a concentration of 0.1~10 ppm to feed and administering said feed to a fish cultivation water tank.

2. A method for inhibiting the proliferation of Scutica in fish or treating fish infected by Scutica comprising adding a composition containing δ-aminolevulinic acid at a concentration of 0.1~10 ppm to feed and administering said feed to a fish cultivation water tank.

* * * * *